United States Patent [19]

Ong et al.

[11] 4,079,141

[45] Mar. 14, 1978

[54] AZABICYCLOALKANES

[75] Inventors: Helen Hu Ong, Whippany; Vernon Brian Anderson, High Bridge, both of N.J.

[73] Assignee: American Hoechst Corporation, Bridgewater, N.J.

[21] Appl. No.: 732,415

[22] Filed: Oct. 14, 1976

Related U.S. Application Data

[63] Continuation-in-part of Ser. No. 560,510, March 20, 1975, abandoned.

[51] Int. Cl.$^2$ .................. C07D 221/22; A61K 31/445
[52] U.S. Cl. ................................ 424/267; 260/239 B; 260/239 BF; 260/250 BN; 260/293.54; 260/295 R; 260/296 R; 260/326.37; 260/332.2 R; 260/332.3 P; 260/347.4; 260/347.7; 424/244; 424/250; 424/263; 424/274; 424/275; 424/285

[58] Field of Search ...... 260/239 B, 239 BF, 250 BN, 260/295 R, 296 R, 326.37, 332.2 R, 332.3 P, 347.4, 347.7, 293.54; 424/244, 250, 263, 267, 274, 275, 285

[56] References Cited

PUBLICATIONS

May et al., J. Org. Chem. 20: 1197–1201 (1955).
May et al., J. Med. Chem. 13: 805–807 (1970).
May et al., J. Org. Chem. 21: 899–901 (1956).

*Primary Examiner*—Cecilia M. S. Jaisle
*Attorney, Agent, or Firm*—Curtis, Morris & Safford

[57] ABSTRACT

Novel substituted azabicycloalkanes and methods of preparing the same are disclosed. These compounds are useful as analgetic agents which exhibit a tendency towards low physical dependence.

24 Claims, No Drawings

AZABICYCLOALKANES

This is a continuation-in-part of application Ser. No. 560,510, filed Mar. 20, 1975 now abandoned.

This invention relates to novel azabicycloalkanes, their intermediates and the physiological acceptable salts thereof which are useful as analgetic agents that exhibit low physical dependence liability, to methods of preparing the same, to methods of treatment with pharmaceutically effective amounts thereof, and to pharmaceutical compositions containing such compounds as essential active ingredients.

To the best of our knowledge the compounds of this invention have heretofore neither been described nor suggested. Some 5-(3-hydroxyphenyl)morphans are known to display significant morphine-like analgesic activity with low physical dependence liability. The above has been reported in E. L. May and J. G. Murphy, J. Org. Chem., 19, 615 (1954), E. L. May and J. G. Murphy, J. Org. Chem., 20, 1197 (1955), E. L. May, J. Org. Chem., 21, 899 (1956), E. L. May and M. Takeda, J. Med. Chem., 13, 805 (1970), H. H. Ong, T. Oh-ishi, and E. L. May, J. Med. Chem., 17, 133 (1974) and M. E. Rogers and E. L. May, J. Med. Chem., 17, 1328 (1974). *Medicinal Chemistry*, A. Burger, Ed., Whiley-Interscience, pp 1340-1341, 1970 teaches that many morphinans of the general formula

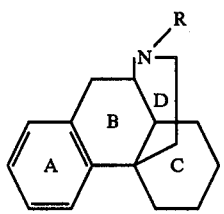

are known to possess morphine-like analgetic activity. Also it is known that reduction in size of the "C" ring of the above morphinans from 6 to 5 members leads to compounds which exhibit no analgesic activity. This ring reduction effect on analgesic activity is described in the article, "The Testing and Development of Analgetic Drugs", by A. H. Becket and A. F. Casey, in Progress in Medicinal Chemistry, G. P. Ellis and G. B. West, Eds, pg 58 (1962). Additionally, Japanese Pat. No. 059129 issued on Nov. 4, 1974 discloses 1-(3-oxyphenyl)-6-substituted-6-azabicyclo(3.2.1)octanes exhibiting activity as analgetics. However, the compounds of the present invention have substantial structural differences and suprisingly good analgetic activity with respect to the prior art.

This invention discloses azabicycloalkanes of the formulae

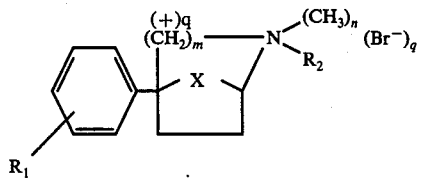

wherein $R_1$ is methoxy, hydroxy or loweralkanoyloxy; $R_2$ is hydrogen, straight or branched chain loweralkyl, loweralkenyl, alkylcycloalkyl of from 4 to 7 carbon atoms, unsubstituted and halogen substituted benzoylloweralkyl in which the subtituents are on the phenyl ring, unsubstituted and substituted phenylloweralkyl in which the substituents are on the phenyl ring and represent chlorine, bromine, fluorine, loweralkoxy, hydroxy, nitro, amino, loweralkyl or acylamino of from 1 to 5 carbon atoms, heteroaryl loweralkyl in which the heteroaryl group is thienyl, furyl, pyridyl pyrrolyl, or pyrazinyl, or a cyano radical; X is $CH_2$ or $C=O$; and $n$ and $q$ are always the same and are the integer 0 or 1; and the pharmaceutically acceptable acid addition salts thereof.

Preferred compounds are those wherein $R_1$ is methoxy, hydroxy or acetoxy; $R_2$ is straight chain loweralkyl, fluorobenzoylalkyl, unsubstituted and substituted phenylalkyl, thienylalkyl, furylalkyl, loweralkenyl or alkylcycloalkyl of from 4 to 7 carbon atoms; X is $CH_2$, and $n$ and $q$ are the integer 0.

Acids useful for preparing the pharmaceutically acceptable acid addition salts of the invention include mineral acids such as hydrochloric, hydrobromic, sulfuric, nitric, phosphoric and perchloric, as well as organic acids such as tartaric, citric, acetic, succinic, maleic, fumaric and oxalic.

The compounds of the present invention are prepared by one of the several multi-step reaction sequences as described below.

Method A

1. A 2-(alkoxyphenyl)cycloalkanone, I, is reacted with a N-dimethylaminoalkyl halide in the presence or absence of a suitable organic solvent, in the presence of a base, for from a few minutes to 24 hours, at a temperature of from ambient to the boiling point of the solvent to provide a 2-(N-dimethylaminoalkyl)-2-(alkoxyphenyl)cycloalkanone, II. A preferred method utilizes potassium tertiary butoxide as the base and boiling 1,2-dimethoxyethane as the solvent. It will be readily appreciated by those skilled in the art that the time and temperature necessary to complete the reaction in this and subsequent steps are interrelated and dependent upon the structures and compositions of the reaction components and the solvent.

2. A bromoketone, III, is prepared by the bromination of an above cycloalkanone, II, by any suitable method known to the art. One preferred method is reacting a cycloalkanone with a solution of bromine in glacial acetic acid at a temperature of from ambient to 100° C.

3. A quaternary salt, IV, is prepared by cyclizing the above bromoketone, III, by a method known to the art. One such method is the treatment of an inorganic acid addition salt of the ketone with a mixture of ammonium hydroxide and diethyl ether.

4. The quaternary salt, IV, is converted to an oxo-2-azabicyclo compound, V. One preferred method is pyrolysis in the presence or absence of a high boiling solvent such as nonanol.

5. The oxo-2-azabicyclo compound, V, is reduced by a method known to the art to provide the corresponding 2-azabicyclo compound, VI. One preferred method is subjecting the oxo-2-azabicyclo compound to the conditions of the Wolff-Kishner reduction.

6. The 2-azabicyclo compound, VI, is converted to the corresponding secondary amine by any method known to the art. One preferred method is by reaction with cyanogen bromide. A corresponding secondary amine, VII, is obtained on hydrolysis of the cyano group. One such method involves utilization of an acid such as dilute hydrochloric acid.

7. An above secondary amine, VII, is reconverted to a corresponding tertiary amine, VIII, by either alkylation or acylation followed by reduction. Said conversion is effected in the presence or absence of a solvent, such as dimethylformamide, an acid scavenger such as sodium bicarbonate, an inert atmosphere such as nitrogen, and a catalyst such as potassium iodide and at a temperature from ambient to the boiling point of the solvent, for from several minutes to 24 hours. When a secondary amine is acylated the acyl compound is reduced to the corresponding alkyl or aralkyl compound. One method of reduction utilizes lithium aluminum hydride as the reducing agent.

The alkoxy group of any compounds of the invention can be dealkylated by a method known to the art to provide a corresponding phenolic compound. A preferred method is dealkylating with refluxing concentrated hydrobromic acid, under an inert atmosphere such as nitrogen, for from a few minutes to several hours.

A phenolic compound can be acylated to a corresponding ester. Preferred acylating agents are acyl halides and anhydrides with or without an additional base such as triethylamine or potassium carbonate and with or without a solvent such as chloroform.

Compounds of the invention are useful as analgesic agents due to their ability to alleviate pain in mammals. The analgesic utility of compounds of this invention is demonstrated in the 2-phenyl-1,4-quinone induced writhing assay in mice, a standard assay for analgesia [Proc. Soc. Exptl. Biol. Med., 95, 729 (1957)]. Thus, for example, an approximately 50% inhibition in writhing was effected 30 minutes after subcutaneous administration by a 0.35 mg/kg of body weight ($ED_{50}$) of 2-[3-(4-fluorobenzoyl)propyl]-5-(3-hydroxyphenyl)-2-azabicyclo[3.2.1]octane. $ED_{50}$'s, measured at corresponding post drug times, of various other compounds of the invention are outlined below in Table I.

TABLE I

| | Drug Administration Time (minutes) | $ED_{50}$ mg/kg |
|---|---|---|
| 5-(3-hydroxyphenyl)-2-phenethyl 2-azabicyclo[3.2.1]octane.HBr | 15 | 0.7 |
| 2-[3-(4-fluorobenzoyl)propyl]-5-(3-methoxyphenyl)-2-azabicyclo-[3.2.1]octane.HBr | 60 | 0.7 |
| 2-n-butyl-5-(3-methoxyphenyl)-2-azabicyclo[3.2.1]octane.HBr | 30 | 4.6 |
| 2-n-amyl-5-(3-methoxyphenyl)-2-azabicyclo[3.2.1]octane.HBr | 30 | 5.0 |
| 5-(3-methoxyphenyl)-2-phenethyl-2-azabicyclo[3.2.1]octane.HBr | 30 | 5.9 |
| 2-cyclopropylmethyl-5-(3-hydroxyphenyl)-2-azabicyclo[3.2.1]octane.HBr | 30 | 6.0 |
| 5-(3-acetoxyphenyl)-2-phenethyl-2-azabicyclo[3.2.1]octane.HBr | 30 | 6.1 |
| 5-(3-methoxyphenyl)-2-n-propyl-2-azabicyclo[3.2.1]octane.HBr | 15 | 7.4 |
| 5-(3-methoxyphenyl)-2-methyl-2-azabicyclo[3.2.1]octane.HBr | 30 | 7.9 |
| 5-(3-hydroxyphenyl)-2-n-propyl-2-azabicyclo[3.2.1]octane.HBr | 15 | 8.9 |
| 2-n-butyl-5-(3-hydroxyphenyl)-2-azabicyclo[3.2.1]octane.HBr | 15 | 9.0 |
| 5-(3-hydroxyphenyl)-2-methyl-2-azabicyclo[3.2.1]octane.HBr | 30 | 9.5 |
| 2-n-amyl-5-(3-hydroxyphenyl)-2-azabicyclo[3.2.1]octane.HBr | 30 | 11.0 |
| 2-(2-furylmethyl)-5-(3-hydroxyphenyl)-2-azabicyclo[3.2.1]octane.HBr | 15 | 22.0 |

For comparison, morphine exhibits an $ED_{50}$ of 0.47 mg/kg after 30 minutes and pentazocine, a recognized effective analgesic agent and morphine antagonist exhibits $ED_{50}$'s of 1.5 mg/kg after 15 minutes and 4.8 mg/kg after 30 minutes.

The compounds of the present invention also exhibit good morphine antagonist properties. Accordingly while the compounds of the invention are potent analgetics they also exhibit low physical dependence properties. The morphine antagonist properties are demonstrated in the following procedure. A sample of 25 mg/kg of body weight of morphine sulfate and the compound of the invention to be tested are concurrently administered subcutaneously to 10 pairs of mice. The mice are then observed for inhibition of the characteristic mania (increased motor activity) normally produced in mice by morphine. Results are outlined in Table II and expressed as percent of pairs in which the mania is inhibited at a given dose level.

TABLE II

| | Dose (mg/kg) | % Inhibition |
|---|---|---|
| 5-(3-methoxyphenyl)-2-methyl-2-azabicyclo[3.2.1]octane.HBr | 50 | 50 |
| 5-(3-hydroxyphenyl)-2-methyl-2-azabicyclo[3.2.1.]octane.HBr | 50 | 80 |
| 5-(3-acetoxyphenyl)-2-methyl-2-azabicyclo[3.2.1]octane.HBr | 50 | 100 |
| 5-(3-hydroxyphenyl)-2-phenethyl-2-azabicyclo[3.2.1]octane.HBr | 50 | 100 |
| | 1 | 50 |
| 5-(3-methoxyphenyl)-2-n-propyl-2-azabicyclo[3.2.1]octane.HBr | 50 | 100 |
| | 10 | 50 |
| 5-(3-hydroxyphenyl)-2-n-propyl-2-azabicyclo[3.2.1]octane.HBr | 50 | 100 |
| 2-cyclopropylmethyl-5-(3-hydroxyphenyl)-2-azabicyclo[3.2.1]octane.HBr | 25 | 100 |
| 2-n-amyl-5-(3-hydroxyphenyl)-2-azabicyclo[3.2.1]octane.HBr | 25 | 100 |
| | 3 | 50 |
| 2-n-amyl-5-(3-methoxyphenyl)-2-azabicyclo[3.2.1]octane.HBr | 30 | 100 |
| 2-(2-furylmethyl)-5-(3-hydroxyphenyl)-2-azabicyclo[3.2.1]octane.HBr | 25 | 100 |
| 2-n-butyl-5-(3-hydroxyphenyl)-2-azabicyclo[3.2.1]octane.HBr | 25 | 100 |
| 2-n-butyl-5-(3-methoxyphenyl)-2-azabicyclo[3.2.1]octane.HBr | 25 | 100 |
| 2-[3-(4-fluorobenzoyl)propyl]-5-(3-methoxyphenyl)-2-azabicyclo[3.2.1]octane.HBr | 10 | 100 |
| 2-[3-(4-fluorobenzoyl)propyl]-5-(3-hydroxyphenyl)-2-azabicyclo[3.2.1]octane.HBr | 10 | 100 |
| 5-(3-acetoxyphenyl)-2-phenethyl-2-azabicyclo[3.2.1]octane.HBr | 10 | 70 |

For comparison, pentazocine, a standard analgetic which is a morphine antagonist, exhibits a 50% inhibition at a dose of >50 mg/kg of body weight.

The above data illustrate that the compounds of the present invention are useful as analgesic agents exhibiting low physical dependence liability when administered in amounts ranging from about 0.1 to 50 mg per kg of body weight per day.

Further examples of compounds of the invention are:

5-(3-hydroxyphenyl)-2-[2-(2-pyridyl)ethyl]-2-azabicyclo]3.2.1]octane;

5-(3-methoxyphenyl)-2-(3-Pyrazinylpropyl)-2-azabicyclo[3.2.1]octane;

2-isopropyl-5-(4-hydroxyphenyl)-2-azabicyclo-[3.2.1]octane;

2-[3-(3-chlorobenzoyl)butyl]-5-(3-methoxyphenyl)-2-azabicyclo[3.2.1]octane;

2-cyclohexylmethyl-5-(3-hydroxyphenyl)-2-azabicyclo[3.2.1]octane;

5-(4-methoxyphenyl)-2-(4-chlorophenethyl)-2-azabicyclo[3.2.1]octane;

2-(3-butenyl)-5-(4-methoxyphenyl)-2-azabicyclo[3.2.1]octane;

6-(3-methoxyphenyl)-2-methyl-2-azabicyclo[4.2.1]nonane;

6-(3-hydroxyphenyl)-2-[3-(nitrophenyl)propyl]-2-azabicyclo[4.2.1]nonane;

2-(4-acetamidophenethyl)-5-(3-hydroxyphenyl)-2-azabicyclo[3.2.1]octane; and 2-(4-aminophenethyl)-5-(3-methoxyphenyl)-2-azabicyclo[3.2.1]octane.

Effective quantities of the compounds of the invention may be administered to a patient by any one of various methods, for example, orally as in capsules or tablets, parenterally in the form of sterile solutions or suspensions, and in some cases intraveneously in the form of sterile solutions. The free base final products, while effective themselves, may be formulated and administered in the form of their pharmaceutically acceptable addition salts for purposes of stability, convenience of crystallization, increased solubility and the like.

The active compounds of the present invention may be orally administered, for example, with an inert diluent or with an edible carrier, or they may be enclosed in gelatin capsules, or they may be compressed into tablets. For the purpose of oral therapeutic administration, the active compounds of the invention may be incorporated with excipients and used in the form of tablets, troches, capsules, elixirs, suspensions, syrups, wafers, chewing gum and the like. These preparations should contain at least 0.5% of active compound, but may be varied depending upon the particular form and may conveniently be between 4% to about 70% of the weight of the unit. The amount of active compound in such compositions is such that a suitable dosage will be obtained. Preferred compositions and preparations according to the present invention are prepared so that an oral dosage unit form contains between 1.0-300 milligrams of active compound.

The tablets, pills, capsules, troches, and the like may also contain the following ingredients: a binder such as microcrystalline cellulose, gum tragacanth or gelatin; an excipient such as starch or lactose, a disintegrating agent such as alginic acid, Primogel, corn starch and the like; a lubricant such as magnesium stearate or Sterotex; a glidant such as colloidal silicon dioxide; and a sweetening agent such as sucrose or saccharin may be added or a flavoring agent such as peppermint, methyl salicylate, or orange flavoring. When the dosage unit form is a capsule, it may contain, in addition to materials of the above type, a liquid carrier such as a fatty oil. Other dosage unit forms may contain other various materials which modify the physical form of the dosage unit, for example, as coatings. Thus, tablets or pills may be coated with sugar, Shellac, or other enteric coating agents. A syrup may contain, in addition to the active compounds, sucrose as a sweetening agent, and certain preservatives, dyes and colorings, and flavors. Materials used in preparing these various compositions should be pharmaceutically pure and non-toxic in the amounts used.

For the purpose of parenteral therapeutics administration, the active compounds of the invention may be incorporated into a solution or suspension. These preparations should contain at least 0.1% of active compound, but may be varied to be between 0.5 and about 30% of the weight thereof. The amount of active compound in such compositions is such that a suitable dosage will be obtained. Preferred compositions and preparations according to the present invention are prepared so that a parenteral dosage unit contains between 0.5 to 100 milligrams of active compound.

The solutions or suspensions may also include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediamine-tetraacetic acid; buffers such as acetates, citrates or phosphates and agents for the adjustment of toxicity such as sodium chloride or dextrose. The parenteral preparation can be enclosed in ampules, disposable syringes or multiple dose vials made of glass or plastic.

The invention is further illustrated by the following examples of intermediates and compounds of the invention, given for illustrative purposes.

EXAMPLE 1 a. 258 ml of butyllithium (2.2M; 5% excess) are slowly added with stirring to a solution of 112 g of 4-bromoanisole in 380 ml of tetrahydrofuran at −60° C., followed by 70.8 g of 2-chlorocyclopentanone in 50 ml of tetrahydrofuran. The reaction mixture is stirred at −50° to −60° C. for an additional hour and then allowed to warm to ambient temperature. Xylene is introduced, and the tetrahydrofuran is slowly distilled off. When the temperature reaches 98°–100° C., the distillation is stopped and the mixture is heated at reflux overnight. The cooled reaction mixture is treated with 1N hydrochloric acid, filtered, and the organic layer separated and washed successively with water, dilute sodium bicarbonate solution and water and dried.

The solvent is removed and the resulting oil is vacuum distilled, the main fraction being the oil, 2-(4-methoxyphenyl)cyclopentanone, b.p. 125°–128° C./0.2mm.

Analysis: Calculated for $C_{12}H_{14}O_2$: 75.77%C; 7.41%H. Found: 75.52%C; 7.43%H.

b. To a slurry of 5.7 g of potassium t-butoxide in 1,2-dimethoxyethane is added dropwise a solution of 9.5 g of 2-(4-methoxyphenyl)cyclopentanone in 10 ml of 1,2-dimethoxyethane. The reaction mixture is stirred at ambient temperature for 30 minutes, 5.4 g of 2-dimethylaminoethyl chloride in 5 ml of 1,2-dimethoxyethane are added and the resulting solution is stirred and refluxed overnight. The solution is cooled, diluted with ether, and extracted with 1N hydrochloric acid. The combined acid extracts are basified, extracted with ether, dried and the ether removed leaving a light orange oil which is distilled at 159°–166° C./0.4mm and converted to the hydrobromide salt of 2-(2-dimethylaminoethyl)-2-(4-methoxyphenyl)cyclopentanone, mp 157°–159° C.

Analysis: Calculated for $C_{16}H_{23}NO_2.HBr$: 56.14%C; 7.02%H; 4.09%N; 23.39% Br. Found: 55.22%C; 6.98%H; 4.01%N; 23.74%Br.

By following the manipulative procedure described above in step a, 41.1 g of 3-bromoanisole, 114 ml of butyllithium (2.2M; 0.25 mole), and 23.7 gm of 2-chlorocyclopentanone are reacted to give a pale yellowish oil, b.p. 125°–127° C/0.3mm., 2-(3-methoxyphenyl)cyclopentanone.

EXAMPLES 2 & 3

By following the manipulative procedure described above in Example 1(b), novel compounds listed in Table III are produced by the reaction of 2-(3-methoxyphenyl)cyclopentanone with 3-dimethylaminopropyl chloride and 2-dimethylaminoethyl chloride respectively.

TABLE III

| Ex. | Empirical Formula | mp/bp(mm) °C | Analysis Calculated |   |   | Found |   |   |
|---|---|---|---|---|---|---|---|---|
|   |   |   | %C | %H | %N | %C | %H | %N |
| 2 | $C_{17}H_{25}NO_2$ | 137–140 (0.2mm) | 74.14 | 9.15 | 5.08 | 74.20 | 9.37 | 4.98 |
| 3 | $C_{16}H_{23}NO_2 \cdot HBr$ | 158–159 | 56.14 | 7.07 | 4.09 | 56.20 | 7.17 | 4.08 |

EXAMPLE 4

A suspension of 1.37 g of 2-(2-dimethylaminoethyl)-2-(3-methoxyphenyl)cyclopentanone (Example 3) in 5 ml of glacial acetic acid is heated gently on a steam bath to effect a clear solution. To the warm stirred solution is slowly added 0.70 g of bromine in 10 ml of glacial acetic acid and the solution is allowed to stand at ambient temperature overnight. The reaction mixture is diluted with ether and an oily residue separates which is crystallized from an acetone-ethyl acetate-ether mixture to give fluffy needles, mp 110°–113° C., of 5-bromo-2-(2-dimethylaminoethyl)-2-(3-methoxyphenyl)cyclopentanone hydrobromide.

Analysis: Calculated for $C_{16}H_{22}BrNO_2 \cdot HBr$: 45.63%C; 5.50%H; 3.32%N. Found: 46.49%C; 5.77%H; 3.21%N.

In addition 2-(3-dimethylaminopropyl)-2-(3-methoxyphenyl)cyclopentanone (Example 2) can be treated according to the above procedure to give 5-bromo-2-(3-dimethylaminopropyl)-2-(3-methoxyphenyl)cyclopentanone.

EXAMPLE 5

A solution of 1.71 g of 2-(2-dimethylaminoethyl)-2-(4-methoxyphenyl)cyclopentanone (Example 1) in 15 ml of chloroform is cooled to 5° C. and to it is added dropwise a solution of 0.80 g of bromine in 15 ml of chloroform. The reaction mixture is allowed to stir overnight. The solvent and excess bromine are removed under reduced pressure, leaving a glassy residue which is recrystallized from an acetone-ethyl acetate mixture to give crystals, mp 146°–147° C., dec, of 5-bromo-2-(2-dimethylaminoethyl)-2-(4-methoxyphenyl)cyclopentanone hydrobromide.

Analysis: Calculated for $C_{16}H_{22}BrNO_2 \cdot HBr$: 45.63%C; 5.50%H; 3.32%N; 37.93%Br Found: 45.72%C; 5.59%H; 3.44%N; 37.67%Br

EXAMPLE 6

To a suspension of 0.88 g of 5-bromo-2-(2-dimethylaminoethyl)-2-(3-methoxyphenyl)cyclopentanone hydrobromide (Example 4) in 50 ml of ether and 10 ml of water is added dropwise 0.8 ml of concentrated ammonia. The mixture is shaken vigorously and the ether layer is separated. The ether layer is dried, and the ether removed leaving a semi-solid residue. Acetone is added to the residue and the mixture is stirred at reflux for 2 hrs. Upon cooling, the quaternary salt precipitates from the acetone and is recrystallized from absolute ethanol to give colorless prisms, mp 244°–245° C., dec of 5-(3-methoxyphenyl)-2-methyl-8-oxo-2-azabicyclo[3.2.1]octane methobromide.

Analysis: Calculated for $C_{16}H_{22}BrNO_2$: 56.75%C; 6.52%H; 4.11%N; 23.48%Br. Found: 56.48%C; 6.59%H; 3.98%N; 23.30%Br.

In addition 5-bromo-2-(3-dimethylaminopropyl)-2-(3-methoxyphenyl)cyclopentanone can be treated according to the above procedure to give 6-(3-methoxyphenyl)-2-methyl-9-oxo-2-azabicyclo[4.2.1]nonane methobromide.

EXAMPLE 7

A solution of 1.7 g of 5-bromo-2-dimethylaminoethyl-2-(4-methoxyphenyl)cyclopentanone hydrobromide (Example 5) in 10 ml of water is stirred vigorously while 1 ml of concentrated ammonia is added dropwise. Crystals begin to deposit after a few minutes and stirring is continued for an additional 2 hours. The mixture is filtered and the residue is dried and recrystallized from 95% ethanol to give shiny plates, mp 255°–258° C., dec, of 5-(4-methoxyphenyl)-2-methyl-8-oxo-2-azabicyclo[3.2.1]octane methobromide.

Analysis: Calculated for $C_{16}H_{22}BrNO_2$: 56.47%C; 6.52%H; 4.11%N; 23.48%Br Found: 56.30%C; 6.53%H; 4.03%N; 23.35%Br

EXAMPLE 8

1.4 g of finely powdered 5-(3-methoxyphenyl)-2-methyl-8-oxo-2-azabicyclo[3.2.1]octane methobromide (Example 6) are pyrolized in vacuo. As the heating bath temperature is raised to 250° C., liquid appears which is rapidly distilled. The condensate is redistilled to give a pale yellowish oil, bp 135°–138° C./0.3mm of 5-(3-methoxyphenyl)-2-methyl-8-oxo-2-azabicyclo[3.2.1]octane.

Analysis: Calculated for $C_{15}H_{19}NO$: 73.44%C; 7.80%H; 5.71%N. Found: 73.16%C; 8.04%H; 5.75%N.

In addition 6-(3-methoxyphenyl)-2-methyl-9-oxo-2-azabicyclo[4.2.1]nonane methobromide is subjected to a similar thermal pyrolysis just above its melting point, to produce 6-(3-methoxyphenyl)-2-methyl-9-oxo-2-azabicyclo[4.2.1]nonane.

EXAMPLE 9

By following a similar procedure to the manipulative procedure outlined above in example 8, 5-(4-methoxyphenyl)-2-methyl-8-oxo-2-azabicyclo[3.2.1]octane methobromide (Example 7) produces an oil. The oil gradually solidifies to give chunky crystals, mp 96°–97° C., of 5-4-methoxyphenyl)-2-methyl-8-oxo-2-azabicyclo[3.2.1]octane.

Analysis: Calculated for $C_{15}H_{19}NO_2$: 73.44%C; 7.80%H; 5.71%N Found: 73.47%C; 7.92%H; 5.71%N

EXAMPLE 10

A mixture of 5.5 g of 5-(3-methoxyphenyl)-2-methyl-8-oxo-2-azabicyclo[3.2.1]octane (Example 8) 5.5 ml of 95% hydrazine hydrate, 5.5 g of potassium hydroxide and 35 ml of triethylene glycol is stirred at a temperature of 160°–165° C. for 4 hours and then at 190° C. for an additional hour. The mixture is cooled, diluted with water and extracted with ether. The combined ether extracts are washed with water, dried, and the ether removed leaving an oil which is converted to the hydrobromide salt and recrystallized from an acetone-ether mixture to give fine needles, mp 175°–177° C., of 5-(3-methoxyphenyl)-2-methyl-2-azabicyclo[3.2.1]octane hydrobromide.

Analysis: Calculated for $C_{15}H_{21}NO \cdot HBr$: 57.70%C; 7.10%H; 4.48%N; 25.58%Br. Found: 57.61%C; 7.12%H; 4.47%N; 25.57%Br.

In addition 6-(3-methoxyphenyl)-2-methyl-9-oxo-2-azabicyclo[4.2.1]nonane is treated according to the above procedure to give 6-(3-methoxyphenyl)-2-methyl-2-azabicy-clo[4.2.1]nonane hydrobromide.

EXAMPLE 11

By following the manipulative procedure outlined above in Example 10, a sample of 5-(4-methoxyphenyl)-2-methyl-8-oxo-2-azabicyclo[3.2.1]octane produces granules, mp 188°–190° C., of 5-(4-methoxyphenyl)-2-methyl-2-azabicyclo[3.2.1]octane hydrobromide.

Analysis: Calculated for $C_{15}H_{21}NO \cdot HBr$: 57.70%C; 7.10%H; 4.48%N; 25.58%Br. Found: 57.41%C; 7.20%H; 4.44%N; 25.63%Br.

EXAMPLE 12

A solution of 4.16 g of 5-(3-methoxyphenyl)-2-methyl-2-azabicyclo[3.2.1]octane (the free base of Example 10) in 35 ml of chloroform is added dropwise to a stirred solution of 2.1 g of cyanogen bromide in 15 ml of chloroform, followed by refluxing for 3 hours and evaporation to dryness. Ethanol is added to the residue and this solution is evaporated to dryness leaving a residue which is recrystallized from an ether-hexane mixture to give needles, mp 96°–97° C., of 2-cyano-5-(3-methoxyphenyl)-2-azabicyclo[3.2.1]octane.

Analysis: Calculated for $C_{15}H_{18}N_2O$: 74.37%C; 7.48%H; 11.56%N. Found: 74.11%C; 7.59%H; 11.59%N.

EXAMPLE 13

A solution of 0.34 g of 2-cyano-5-(3-methoxyphenyl)-2-azabicyclo[3.2.1]octane (Example 12) in 25 ml of 5% hydrocholoric acid is refluxed for 18 hours. The solution is cooled, basified with sodium hydroxide and extracted with ether. The ether solution is dried and concentrated leaving an oil which is converted to its hydrobromide salt. Crystallization from an acetone-ethyl acetate mixture gives colorless crystals, mp 137.5°–138.5° C., of 5-(3-methoxyphenyl)-2-azabicyclo[3.2.1]octane hydrobromide.

Analysis: Calculated for $C_{14}H_{19}NO \cdot HBr$: 56.37%C; 6.76%H; 4.69%N; 26.79%Br. Found: 56.28%C; 6.78%H; 4.60% N; 26.98%Br.

EXAMPLE 14

A mixture of 1.3 g of 5-(3-methoxyphenyl)-2-azabicyclo[3.2.1]octane (the free base of Example 13) 1.0 g of 1-bromopentane, 1.0 g of sodium bicarbonate and 1.1 g of potassium iodide in 15 ml of dimethylformamide is stirred at 80° C. for 16 hours. The mixture is filtered and the filtrate is concentrated leaving an oily residue. The residue is purified by column chromatography over alumina, with ether as the eluant. The thus purified product is converted to the hydrobromide salt and recrystallized from an acetone-ether mixture to give rosettes, mp 144.5°–146.5° C., of 2-n-amyl-5-(3-methoxyphenyl)-2-azabicyclo[3.2.1]octane hydrobromide.

Analysis: Calculated for $C_{19}H_{29}NO \cdot HBr$: 61.95%C; 8.20%H; 3.80%N; 21.69%Br. Found: 61.93%C; 8.27%H; 3.92%N; 22.04%Br.

EXAMPLES 15–17

By following procedures similar to the manipulative procedure outlined above in Example 14, a sample of 5-(3-methoxyphenyl)-2-azabicyclo[3.2.1]octane (the free base of Example 13) is treated with n-propyliodide, 1-bromobutane, and iodoethane, respectively, to give the compounds listed below in Table IV.

TABLE IV

| | | | Analysis | | | | | | | |
|---|---|---|---|---|---|---|---|---|---|---|
| | Empirical | m.p. | Calculated | | | | Found | | | |
| Ex. | Formula | °C. | %C | %H | %N | %Br | %C | %H | %N | %Br |
| 15 | $C_{17}H_{25}NO \cdot HBr$ | 223–224 | 60.00 | 7.70 | 4.11 | 23.47 | 60.06 | 7.89 | 4.03 | 23.60 |
| 16 | $C_{18}H_{27}NO \cdot HBr$ | 216–217 | 61.02 | 7.96 | 3.95 | 22.55 | 60.91 | 8.13 | 3.92 | 22.71 |
| 17 | $C_{16}H_{23}NO \cdot HBr$ | 148–149 | 58.89 | 7.41 | 4.29 | 24.49 | 58.83 | 7.60 | 4.27 | 24.29 |

EXAMPLE 18

To a solution of 1.1 g of 5-(3-methoxyphenyl)-2-azabicyclo[3.2.1]octane (the free base of Example 13) and 0.75 g of triethylamine of 15 ml of chloroform is added dropwise 0.93 g of phenylacetyl chloride. The reaction solution is stirred overnight at ambient temperature, the solution is extracted with 10% hydrochloric acid, 10% sodium hydroxide and water, dried and evaporated to dryness leaving an amide as an oily residue. The amide is reduced to the amine with lithium aluminum hybride. The hydrobromide salt is prepared and recrystallized from a methanol-acetone-ether solution to give silky needles, mp 188°–189° C., of 5-(3-methoxyphenyl)-2-phenethyl-2-azabicyclo[3.2.1]octane hydrobromide.

Analysis: Calculated for $C_{22}H_{27}NO \cdot HBr$: 65.65%C; 7.01%H; 3.48%N. Found: 65.72%C; 6.92%H; 3,37%N.

In addition 2-furylacetyl chloride can be substituted in the above procedure to give 2-[2-(2-furyl)ethyl]-5-(3-methoxyphenyl)-2-azabicyclo[3.2.1]octane.

EXAMPLE 19–24

By following similar procedures to the manipulative procedure outlined above in Example 18, a sample of 5-(3-methoxyphenyl)-2-azabicyclo[3.2.1]octane (the free base of Example 13) is treated with 2-thiencylacetyl chloride, 4-chlorophenylacetyl chloride, 4-methoxyphenylacetyl chloride, 4-methylphenylacetyl chloride, 3-chlorophenylacetyl chloride, and 3,4-dichlorophenylacetyl chloride, respectively, to give the compounds listed below in Table V.

TABLE V.

| Ex. | Empirical Formula | m.p. °C | Calculated %C | %H | %N | %Br | Found %C | %H | %N | %Br |
|---|---|---|---|---|---|---|---|---|---|---|
| 19 | $C_{20}H_{25}NOS \cdot HBr$ | 173–175 | 58.83 | 6.42 | 3.43 | 19.59 | 58.80 | 6.51 | 3.45 | 19.65 |
| 20 | $C_{22}H_{26}ClNO \cdot HBr$ | 204–206 | 60.48 | 6.23 | 3.21 | 18.29 | 60.70 | 6.24 | 3.22 | 18.33 |
| 21 | $C_{22}H_{29}NO_2 \cdot HBr$ | 201–202 | 63.87 | 6.99 | 3.24 | 18.48 | 63.86 | 7.01 | 3.21 | 18.47 |
| 22 | $C_{23}H_{29}NO \cdot HBr$ | 203.5–205.5 | 66.33 | 7.26 | 3.36 | 19.19 | 66.55 | 7.32 | 3.28 | 19.25 |
| 23 | $C_{22}H_{26}ClNO \cdot HBr$ | 225–227 | 60.48 | 6.23 | 3.21 | 18.29 | 60.35 | 6.32 | 3.10 | 18.17 |
| 24 | $C_{22}H_{25}Cl_2NO \cdot HBr$ | 239–240 | 56.05 | 5.56 | 2.97 | 16.95 | 56.19 | 5.51 | 3.07 | 16.87 |

EXAMPLE 25

A mixture of 1.0 g of 5-(3-methoxyphenyl)-2-azabicyclo[3.2.1]octane (the free base of Example 13) 1.5 g of α-chloro-4-fluorobutyrophenone ethylene glycol ketal, 1.0 g of sodium bicarbonate and 1.0 g of potassium iodide in 15 ml of dimethylformamide is stirred at 80° C. for 16 hours. The mixture is filtered and the filtrate concentrated to an oily residue. An ethanolic solution of hydrogen chloride is added and the solution is stirred at ambient temperature until complete hydrolysis of the ketal is effected. The solution is basified and extracted with methylene dichloride, dried and concentrated. The residue is purified by column chromatography over alumina with ether as the eluant. The eluate is concentrated to a colorless oil, converted to a crystalline hydrobromide, and recrystallized from a methanol-ether mixture to give shiny plates, mp 194°–196° C., of 2-[3-(4-fluorobenzoyl)propyl]-5-(3-methoxyphenyl)-2azabicyclo[3.2.1]octane hydrobromide.

Analysis: Calculated for $C_{24}H_{28}FNO_2 \cdot HBr$: 62.34%C; 6.32%H; 3.03%N; 17.28% Br; 4.54%F. Found: 62.39%C, 6.38%H; 2.99%N; 17.51%Br; 4.51%F.

EXAMPLE 26

A suspension of 1.0 g of 5-(3-methoxyphenyl)-2-phenethyl-2-azabicyclo[3.2.1]octane hydrobromide (Example 19) in 15 ml of 48% hydrobromic acid is stirred at reflux for 1 hour. The cooled mixture is filtered to give tannish crystals which are recrystallized from a methanol-acetone mixture to give crystals, mp 212°–213° C., of 5-83-hydroxyphenyl)-2--phenethyl-2-azabicyclo[3.2.1]octane hydrobromide.

Analysis: Calculated for $C_{21}H_{25}NO \cdot HBr$: 64.95%C; 6.75%H; 3.60%N; 20.58%Br. Found: 64.80%C; 6.76%H; 3.48%N; 20.4%Br.

EXAMPLES 27–40

By following the manipulative procedure outlined in Example 26, the phenolic compounds listed in Table VI are prepared.

TABLE VI

| Ex. | Starting Material | Empirical Formula | m.p. °C | Recryst'n Solvent | Calculated %C | %H | %N | Found %C | %H | %N |
|---|---|---|---|---|---|---|---|---|---|---|
| 27 | Ex. 13 | $C_{13}H_{17}NO \cdot HBr$ | 259–260 | EtOH-Et$_2$O | 54.92 | 6.38 | 4.93 | 55.07 | 6.55 | 4.73 |
| 28 | Ex. 16 | $C_{17}H_{25}NO \cdot HBr$ | >260 | MeOH-Et$_2$O | 60.00 | 7.70 | 4.11 | 59.90 | 7.78 | 3.89 |
| 29 | Ex. 17 | $C_{15}H_{21}NO \cdot HBr$ | 249–250 | MeOH-acetone-Et$_2$O | 57.69 | 7.10 | 4.49 | 57.77 | 7.27 | 4.50 |
| 30 | Ex. 25 | $C_{23}H_{26}FNO_2 \cdot HBr$ | 207–208 | MeOH-acetone-Et$_2$O | 61.59 | 6.07 | 3.12 | 61.49 | 6.17 | 3.07 |
| 31 | Ex. 10 | $C_{14}H_{19}NO \cdot HBr$ | 254–255 | MeOH-Et$_2$O | 56.37 | 6.76 | 4.69 | 56.24 | 6.74 | 4.65 |
| 32 | Ex. 15 | $C_{16}H_{23}NO \cdot HBr$ | 251.5–253 | Acetone/MeOH-Et$_2$O | 58.90 | 7.44 | 4.29 | 58.93 | 7.51 | 4.32 |
| 33 | Ex. 14 | $C_{18}H_{27}NO \cdot HBr$ | 235.5–236.5 | MeOH-Et$_2$O | 61.02 | 8.20 | 3.95 | 60.84 | 8.08 | 3.96 |
| 34 | Ex. 19 | $C_{19}H_{23}NOS \cdot HBr$ | 195–197 | MeOH-Et$_2$O | 57.83 | 6.13 | 3.55 | 57.55 | 6.24 | 3.43 |
| 35 | Ex. 11 | $C_{14}H_{19}NO \cdot HBr$ | 214–216 | MeOH-Acetone-Et$_2$O | 56.37 | 6.76 | 4.69 | 56.13 | 6.83 | 4.65 |
| 36 | Ex. 20 | $C_{21}H_{24}ClNO \cdot HBr$ | 266–267 | MeOH-Acetone-Et$_2$O | 59.64 | 5.96 | 3.31 | 59.57 | 6.09 | 3.17 |
| 37 | Ex. 21 | $C_{21}H_{25}NO_2 \cdot HBr$ | 278–279 | MeOH-Acetone-Et$_2$O | 62.38 | 6.48 | 3.46 | 62.51 | 6.51 | 3.48 |
| 38 | Ex. 22 | $C_{22}H_{27}NO \cdot HBr$ | 231–233 | MeOH-Acetone-Et$_2$O | 65.65 | 7.01 | 3.48 | 65.40 | 6.86 | 3.39 |
| 39 | Ex. 23 | $C_{21}H_{24}ClNO \cdot HBr$ | 217–219 | MeOH-Acetone-Et$_2$O | 59.64 | 5.96 | 3.31 | 59.58 | 6.11 | 3.20 |
| 40 | Ex. 24 | $C_{21}H_{23}Cl_2NO \cdot HBr$ | 237–239 | MeOH-acetone-Et$_2$O | 55.16 | 5.29 | 3.06 | 55.28 | 5.30 | 3.14 |

EXAMPLE 41

A suspension of 730 mg of 5-(3-hydroxyphenyl)-2-azabicyclo[3.2.1]octane (the free of Example 27) and 576 mg of sodium bicarbonate in 8 ml of dimethyformamide is stirred for 30 minutes and 388 mg of dimethylallyl bromide in 2 ml of dimethylformamide is added over a 5 minute span. The mixture is stirred, under nitrogen, at 90°–100° C., for 4 additional hours and then filtered. The filtrate is concentrated to a semicrystalline residue which is purified by column chromatography over alumina with ether as the eluant. The purified tertiary amine is converted to its hydrobromide which is recrystallized from an ethanol-ether mixture to give shiny prisms, mp 215°–216° C., dec, of 2-dimethylallyl-5-(3-hydroxyphenyl)-2-azabicyclo[3.2.1]octane hydrobromide.

Analysis Calculated for $C_{18}H_{25}NO \cdot HBr$: 61.36%C; 7.44%H; 3.97%N; 22.68%Br. Found: 61.14%C; 7.52%H; 3.89%N; 22.47%Br.

EXAMPLE 42

By following the manipulative procedure outlined above in Example 14, a mixture of 6.8 g of 5-(3-hydroxyphenyl)-2-azabicyclo[3.2.1]octane hydrobromide (Example 27) 1.2 g of anhydrous potassium carbonate, 0.38 g of cyclopropylmethyl bromide and a few crystals of potassium iodide in 10 ml of dimethylformamide produces off-white crystals, mp 252°–253° C., of 2-cyclopropylmethyl-5-(3-hydroxphenyl)-2-azabicyclo[3.2.1]-octane hydrobromide.

Analysis: Calculated for $C_{17}H_{23}NO.HBr$: 60.36%C; 7.15%H; 4.14%N; 23.62%Br. Found: 60.19%C; 7.23%H; 3.96%N; 23.61%Br.

EXAMPLE 43

A suspension of 1.13 g of 5-(3-hydroxyphenyl)-2-azabicyclo[3.2.1]octane hydrobromide (Example 27) 5 ml of triethylamine and 8 ml of chloroform is stirred and treated dropwise with 0.67 g of 2-furoyl chloride. After total addition the mixture is stirred overnight at ambient temperature. The reaction mixture is concentrated to dryness, chloroform added, the chloroform solution washed successively with dilute hydrochloric acid, dilute sodium bicarbonate, and water, and dried. The solvent is removed, and the residual amide is reduced with a solution of lithium aluminum hydride in tetrahydrofuran and a hydrobromide prepared which is recrystallized from a methanol-ether mixture to give granules, mp 226°–228° C., of 2-(2-furylmethyl)-5-(3-hydroxyphenyl)-2-azabicyclo[3.2.1]octane hydrobromide.

Analysis: Calculated for $C_{18}H_{21}NO_2$. HBr: 59.34%C; 6.08%H; 3.84%N; 21.93%Br. Found: 59.06%C; 5.89%H; 3.75%N; 21.49%Br.

In addition, by following the above manipulative procedure, substituting 2-furylacetyl chloride for 2-furoyl chloride produces 2-[2-(2-furyl)ethyl]-5-(3-hydroxyphenyl)-2-azabicyclo[3.2.1]octane.

EXAMPLE 44

The free base prepared from 0.5 g of 5-(3-hydroxyphenyl)-2-methyl-2-azabicyclo[3.2.1]octane hydrobromide (Example 31) is heated with 10 ml of acetic anhydride at 90°–100° C. for 1 hour. The liquid is removed leaving a residue that is converted to the hydrobromide salt and is recrystallized from an acetone-ethyl acetate mixture to give white crystals, mp 152°–153° C., of 5-(3-acetoxyphenyl)-2-methyl-2-azabicyclo[3.2.1]-octane hydrobromide.

Analysis:

Calculated for $C_{16}H_{21}NO_2$. HBr: 56.47%C; 6.51%H; 4.11%N; 23.48%Br. Found: 56.29%C; 6.59%H; 4.09%N; 23.54%Br.

EXAMPLE 45

By following the manipulative procedure outlined above in Example 10, 5.0 g of 2-(3-dimethylaminopropyl)-2-(3-methoxyphenyl)cyclopentanone (Example 2) produces an oil which is distilled to a colorless oil, bp 120°–122° C./0.33mm., of 1-(3-dimethylaminopropyl)-1-(3-methoxyphenyl)cyclopentane.

Analysis: Calculated for $C_{17}H_{27}NO$; 78.12%C; 10.41%H; 5.36%N. Found: 77.95%C; 10.55%H; 5.44%N.

EXAMPLE 46

A solution of 2.50 g of 2-(2-dimethylaminoethyl)-2-(4-methoxyphenyl)cyclopentanone (Example 4) 3 ml of 95% hydrazine hydrate and 20 ml of triethylene glycol is treated according to the manipulative procedure of example 10, to produce an oil. The oil is converted to the white fumarate salt, mp 157°–158° C., 1-(2-dimethylamioethyl)-1-(4--methoxyphenyl)cyclopentane fumarate.

Analysis: Calculated for $C_{16}H_{25}NO.C_4H_4O_4$: 66.09%C; 8.04%H; 3.85%N. Found: 66.42%C; 8.10%H; 3.78%N.

EXAMPLE 47

By following the manipulative procedure described above in Example 10, 8.0 g of 2-(2-dimethylaminoethyl)-2-(3-methoxyhenyl)cyclopentaneone (the free base of Example 3) 8 ml of 95% hydrazine hydrate, 8.0 g of potassium hydroxide and 60 ml of triethylene glycol to give a colorless oil, bp 110°–112° C./0.33mm., of 1-(2-dimethylaminoethyl)-1-(3-methoxyphenyl)cyclopentane. The hydrobromide is prepared and recrystallized from a methanol-acetone-ether mixture to give shiny plates, mp 170°–172° C.

Analysis: Calculated for $C_{16}H_{25}NO.HBr$: 58.54%C; 7.98%H; 4.26%N; 24.34%Br. Found: 58.33%C; 7.97%H; 4.25%N; 24.32%Br.

EXAMPLE 48

By following the manipulative procedure outlined above in Example 12, a solution of 5.43 g of 1-(2-dimethylaminoethyl)-1-(4-methoxyphenyl)cyclopentane (the free base of Example 46) in chloroform is added to a stirred solution of 2.57 g of cyanogen bromide in chloroform to give an oil. The oil is dissolved in chlorofrom, subjected to column chromatography with a silica gel column and eluted with ether to produce an orange oil of 1-(N-cyano-N-methylaminoethyl)-1-(4-methoxyphenyl)cyclopentane.

Analysis: Calculated for $C_{16}H_{22}N_2O$: 74.38%C 8.58%H; 10.85%N. Found: 74.02%C; 8.67%H; 10.73%N.

EXAMPLE 49

By following the manipulative procedure outlined above in Example 13, a solution of 4.24 g of 1-(N-cyano-N-methylaminoethyl)-1-(4-methoxyphenyl)cyclopentane (Example 48) and 40 ml of 5% hydrochloric acid is treated to give the white salt, mp 158°–159° C., of 1-(4-methoxyphenyl)-1-(2-methylaminoethyl)cyclopentane hydrobromide.

Analysis: Calculated for $C_{15}H_{23}NO.HBr$: 57.32%C; 7.70%H; 4.46%N. 25.43%Br. Found: 57.04%C; 7.72%H; 4.41%H; 25.51%Br.

EXAMPLE 50

By following sequentially the manipulative procedures outlined above in Examples 12 and 13, a sample of 1-(3-dimethylaminopropyl)-1-(3-methoxyphenyl)cyclopentane (Example 45) is converted to the solid, mp 106.5°–108° C., 1-(3-methoxyphenyl)-1-(3-methylaminopropyl)cyclopentane hydrochloride.

Analysis: Calculated for $C_{16}H_{25}NO.HCl$: 67.71%C; 9.23%H; 4.92%N; 12.49%Cl. Found: 67.14%C; 9.42%H; 4.82%N; 12.71%Cl.

EXAMPLE 51

By following the manipulative procedure outlined above in Examples 48 and 49, 2.5 g of 1-(2-dimethylaminoethyl)-1-(3-methoxyphenyl)cyclopentane hydrobromide (Example 47) produces a hydrobromide which is recrystallized from an acetone-ether mixture to give shiny plates, mp 143°–144° C., of 1-(3-methoxyphenyl)-1-(2-methylaminoethyl)cyclopentane hydrobromide.

Analysis: Calculated for C₁₅H₂₃NO.HRr: 57.33%C; 7.69%H; 4.45%N; 25.42%Br. Found: 57.19%C; 7.63%H; 4.40%N; 25.50%Br.

EXAMPLES 52–58

By following the manipulative procedure outlined above in Example 26, the phenolic compounds listed in Table VI are prepared.

EXAMPLE 62

A mixture of 1.6 g of 5-(3-hydroxyphenyl)-2-phenethyl-2-azabicyclo[3.2.1]octane (free base of Example 26), and 100 ml of acetic anhydride is heated at 100° C for 30 minutes. 50 ml of methanol are added and the reaction mixture is evaporated to dryness. The residue is triturated with anhydrous ether and then treated with ethe-

TABLE VII

| Ex. | Starting Material | Empirical Formula | m.p. °C | Recryst'n Solvent | Analysis Calculated %C | %H | %N | Found %C | %H | %H |
|---|---|---|---|---|---|---|---|---|---|---|
| 52 | Ex. 1b | C₁₅H₂₁NO₂ * | 152.2–154.5 | Acetone-Hexane | 72.86 | 8.55 | 5.66 | 73.01 | 8.68 | 5.52 |
| 53 | Ex. 3 | C₁₅H₂₁NO₂.HBr | 212–213 | MeOH-acetone-Et₂O | 54.88 | 6.75 | 4.26 | 54.62 | 6.89 | 4.18 |
| 54 | Ex. 47 | C₁₅H₂₃NO.HBr | 158–160 | Acetone-Et₂O | 57.33 | 7.69 | 4.45 | 57.19 | 7.86 | 4.41 |
| 55 | Ex. 45 | C₁₆H₂₅NO.HBr | 110–112 | Acetone | 58.54 | 7.98 | 4.26 | 58.81 | 8.10 | 4.11 |
| 56 | Ex. 50 | C₁₅H₂₃NO.HBr | 136–138 | Acetone-Et₂O | 57.33 | 7.69 | 4.45 | 57.56 | 7.92 | 4.29 |
| 57 | Ex. 46 | C₁₅H₂₃NO.HBr | 227–228 | MeOH-Acetone-Et₂O | 57.33 | 7.69 | 4.45 | 57.05 | 7.82 | 4.47 |
| 58 | Ex. 49 | C₁₄H₂₁NO.HBr | 171–172 | MeOH-Acetone-Et₂O | 56.00 | 7.39 | 4.67 | 55.81 | 7.37 | 4.54 |

*Compound converted to free base by basifying the hydrobromic solution.

EXAMPLE 59

By following the manipulative procedure outlined above in Example 18, a solution of 1.7 g of 1-(3-hydroxyphenyl)-1-(3-methylaminopropyl)cyclopentane (the free base of Example 56) 2.4 g of triethylamine in 30 ml chloroform and 2.2 g of cyclopropylcarbonyl chloride in 5 ml of chloroform are reacted to produce the crude hydrochloride which is recrystallized from an acetone-ether mixture to give rhombic crystals, mp 93°–94° C., of 1-[3-(N-cyclopropylmethyl-N-methyl)aminopropyl]-1-(3-hydroxyphenyl)cyclopentane hydrochloride.

Analysis:
Calculated for C₁₉H₂₉NO.HCl: 70.45%C; 9.93%H; 4.33%N. Found: 70.37%C; 9.42%H; 4.30%N.

EXAMPLE 60

By following the manipulative procedure outlined above in Example 25, substituting 1-(2-dimethylaminoethyl)-1-(4-methoxyphenyl)cyclopentane (the free base of Example 49) for 5-(3-methoxyphenyl)-2-azabicyclo[3.2.1]octane produces the salt, mp 144–145° C., of 1-{N-[3-(4-fluorobenzoyl)propyl]-N-methylaminoethyl{-1-(4-methoxyphenyl)-cyclopentane hydrobromide.

Analysis: Calculated for C₂₅H₃₂FNO₂.HBr: 62.76%C; 6.95%H; 2.93%N. Found: 63.01%C; 7.03%H; 2.86%N.

EXAMPLE 61

A mixture of 2.0 g of 1-{N-[3-(4-fluorobenzoyl)propyl]-N-methylaminoethyl}-1-(4-methoxyphenyl)cyclopentane hydrobromide (Example 60) and 20 ml of 48% hydrobromic acid is refluxed for 1 hour. Then the mixture is diluted with ice water and evaporated. The residue is dissolved in 30 ml of 200 proof ethanol and 15 ml of chloroform, and the mixed solvent removed leaving a tan solid which is triturated with ether, filtered and dried to give a solid. The solid is recrystallized from a methanol-acetone-ether mixture to give the product, mp 191°–192° C., of 1-{N-[3-(4-fluorobenzoyl)propyl]N-methylaminoethyl}-1-(4-hydroxyphenyl)cyclopentane hydrobromide.

Analysis: Calculated for C₂₄H₃₀FNO₂.HBr: 62.06%C; 6.73%H; 3.02%N. Found: 62.08%C; 6.78%H; 2.91%N.

real hydrobromic acid to form crystals of 5-(3-acetoxyphenyl)-2-phenethyl-2-azibicyclo[3.2.1]octane-hydrobromide.

Analysis: Calculated for C₂₃H₂₇NO₂.HBr: 64.17%C; 6.56%H; 3.25%N; 18.57%Br. Found: 64.05%C; 6.55%H; 3.20%N; 18.56%Br.

By following the manipulative procedure of this Example 62, substituting propionic anhydride and valeric anhydride for acetic anhydride provides 5-(3-propionyloxyphenyl)-2-phenethyl-2-azabicyclo[3.2.1]octane-hydrobromide and 5-(3-valeroyloxyphenyl)-2-phenethyl-2-azabicyclo[3.2.1]-octane-hydrobromide, respectively.

We claim:

1. A compound of the formula

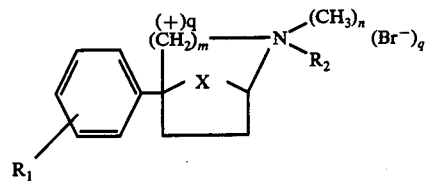

wherein R₁ is methoxy, hydroxy or lower alkanoyloxy; R₂ is hydrogen, straight or branched chain lower alkyl, lower alkenyl, alkylcycloalkyl of from 4 to 7 carbon atoms, unsubstituted and halogen substituted benzoyl lower alkyl in which the substituents are on the phenyl ring, unsubstituted and substituted phenyl lower alkyl in which the substituents are on the phenyl ring and represent chlorine, bromine, fluorine, lower alkoxy, hydroxy, nitro, amino, lower alkyl or lower acyl amino, heteroaryl lower alkyl in which the heteroaryl group is thienyl, furyl, pyridyl, pyrrolyl or pyrazinyl, or a cyano radical; X is CH₂ or C=O; m is the integer 2 or 3; and n and q are always the same and are the integer 0 or 1; or a pharmaceutically acceptable acid addition salt thereof.

2. The compound as defined in claim 1, wherein R₁ is methoxy, hydroxy or acetoxy; R₂ is hydrogen, straight chain alkyl of from 1 to 5 carbon atoms, dimethylallyl, cyclopropylmethyl, 4-fluorobenzoylpropyl, unsubstituted and substituted phenylethyl in which the substituents are on the phenyl ring and represent chlorine, methoxy, hydroxy, or methyl, thienylethyl, furylethyl or a cyano radical; X is CH$_2$; m is the integer 2 and n and q are both the integer 0; or a pharmaceutically acceptable acid addition salt thereof.

3. The compound as defined in claim 1 which is 5-(3-hydroxyphenyl)-2-n-propyl-2-azabicyclo[3.2.1] octane or a pharmaceutically acceptable acid addition salt thereof.

4. The compound as defined in claim 1 which is 2-n-amyl-5-(3-hydroxyphenyl)-2-azabicyclo[3.2.1]octane or a pharmaceutically acceptable acid addition salt thereof.

5. The compound as defined in claim 1 which is 2-cyclopropylmethyl-5-(3-hydroxyphenyl)-2-azabicyclo[3.2.1]octane or a pharmaceutically acceptable acid addition salt thereof.

6. The compound as defined in claim 1 which is 5-(3-methoxyphenyl)-2-phenethyl-2-azabicyclo[3.2.1]octane or a pharmaceuticaly acceptable acid addition salt thereof.

7. The compound as defined in claim 1 which is 5-(3-hydroxyphenyl)-2-phenethyl-2-azabicyclo[3.2.1]octane or a pharmaceutically acceptable acid addition salt thereof.

8. The compound as defined in claim 1 which is 5-(3-methoxyphenyl)-2-azabicyclo[3.2.1]octane, or a pharmaceutically acceptable acid addition salt thereof.

9. The compound as defined in claim 1 which is 5-(3-hydroxyphenyl)-2-azabicyclo[3.2.1]octane or a pharmaceutically acceptable acid addition salt thereof.

10. The compound as defined in claim 1 which is 5-(3-acetoxyphenyl)-2-methyl-2-azabicyclo[3.2.1]octane or a pharmaceutically acceptable acid addition salt thereof.

11. The compound as defined in claim 1 which is 2-n-butyl-5-(3-hydroxyphenyl)-2-azabicyclo[3.2.1]octane or a pharmaceutically acceptable acid addition salt thereof.

12. The compound as defined in claim 1 which is 2-(2-furylmethyl)-5-(3-hydroxyphenyl)-2-azabicyclo[3.2.1]octane or a pharmaceutically acceptable acid addition salt thereof.

13. The compound as defined in claim 1 which is 5-(3-hydroxyphenyl)-2-[-(2-thienyl)ethyl]-2-azabicyclo[3.2.1]octane or a pharmaceutically acceptable acid addition salt thereof.

14. The compound as defined in claim 1 which is 2-ethyl-5-(3-hydroxyphenyl)-2-azabicyclo[3.2.1]octane or a pharmaceutically acceptable acid addition salt thereof.

15. The compound as defined in claim 1 which is 2-[3-(4-fluorobenzoyl)propyl]-5-(3-methoxyphenyl)-2-azabicyclo [3.2.1]octane or a pharmaceutically acceptable acid addition salt thereof.

16. The compound as defined in claim 1 which is 2-[3-(4-fluorobenzoyl)propyl]-5-(3-hydroxyphenyl)-2-azabicyclo[3.2.1]octane or a pharmaceutically acceptable acid addition salt thereof.

17. The compound as defined in claim 1 which is 5-(4-hydroxyphenyl)-2-methyl-2-azabicyclo[3.2.1]octane or a pharmaceutically acceptable acid addition salt thereof.

18. The compound as defined in claim 1 which is 2-(4-chlorophenethyl)-5-(3-hydroxyphenyl)-2-azabicyclo[3.2.1]octane or a pharmaceutically acceptable acid addition salt thereof.

19. The compound as defined in claim 1 which is 2-(3,4-dichlorophenethyl)-5-(3-hydroxyphenyl)-2-azabicyclo [3.2.1] octane or a pharmaceutically acceptable acid addition salt thereof.

20. The compound as defined in claim 1 which is 2-(3-chlorophenethyl)-5-(3-hydroxyphenyl)-2-azabicyclo[3.2.1]octane or a pharmaceutically acceptable acid addition salt thereof.

21. The compound as defined in claim 1 which is 2-[2-(2-furyl)ethyl]-5-(3-hydroxyphenyl)-2-azabicyclo[3.2.1]octane or a pharmaceutically acceptable acid addition salt thereof.

22. The compound as defined in claim 1 which is 5-(3-acetoxyphenyl)-2-phenethyl-2-azabicyclo[3.2.1]octane or a pharmaceutically acceptable acid addition salt thereof.

23. A method of effecting analgesia which comprises administering to a patient in need of such treatment an analgetically effective amount of a compound or salt as defined in claim 1.

24. An analgestic composition which comprises between about 0.5 and about 70 percent by weight of a compound or salt as defined in claim 1 as an essential active ingredient, the balance being a pharmaceutically acceptable carrier therefor.

* * * * *

UNITED STATES PATENT AND TRADEMARK OFFICE
CERTIFICATE OF CORRECTION

PATENT NO. : 4,079,141
DATED : March 14, 1978
INVENTOR(S) : Helen Hu Ong and Vernon Brian Anderson It is certified that error appears in the above-identified patent and that said Letters Patent are hereby corrected as shown below:

Column 4, line 60: "...clo]3.2.1]..." should be
--...clo[3.2.1]...--;

Column 8, line 59: "5-4-methoxy..." should be
--5-(4-methoxy...--;

Column 9, line 16: "...azabicy-clo..." should be
--...azabicyclo...--;

Column 10, line 48: "hybride" should be --hydride--;

Column 10, line 54: "3,37%N" should be --3.37%N--;

Column 11, Table V: Under Calculated: Second %H should be
--%N--;

Column 11, line 54: "...-2azabicy-..." should be
--...-2-azabicy-...--;

Column 11, line 67: "5-83-hydroxy..." should be
--5-(3-hydroxy...--;

Column 12, line 14: "20.4%Br" should be --20.47%Br--;

Column 13, line 67: "...amioethyl)-1-(4--methoxy..." should be
--...aminoethyl)-1-(4-methoxy...--;

Column 14, line 8: "...methoxyhenyl)cyclopentaneone..."
should be
--...methoxyphenyl)cyclopentanone--;

UNITED STATES PATENT AND TRADEMARK OFFICE
CERTIFICATE OF CORRECTION

PATENT NO. : 4,079,141
DATED : March 14, 1978
INVENTOR(S) : Helen Hu Ong and Vernon Brian Anderson It is certified that error appears in the above-identified patent and that said Letters Patent are hereby corrected as shown below:

Column 15, line 48: "...ethyl{-1-(4-methoxyphenyl)-cyclopentane" should be
--...ethyl}-1-(4-methoxyphenyl)cyclopentane--;

Column 16, line 26: "...azibicyclo..." should be --azabicyclo..--

Column 16, line 36: "...[3.2.1]-octane-hydro..." should be
--...[3.2.1]octane·hydro...--;

Claim 13, line 44: "...-2-[-(2-..." should be --...-2-[2-(2-...--

Claim 19, line 23: "...cyclo   [3.2.1]   octane" should be closed up to read
--...cyclo[3.2.1]octane--;

UNITED STATES PATENT AND TRADEMARK OFFICE
CERTIFICATE OF CORRECTION

PATENT NO. : 4,079,141
DATED : March 14, 1978
INVENTOR(S) : Helen Hu Ong and Vernon Brian Anderson It is certified that error appears in the above-identified patent and that said Letters Patent are hereby corrected as shown below:

Claim 1, Column 1, the Second structure should read as follows:

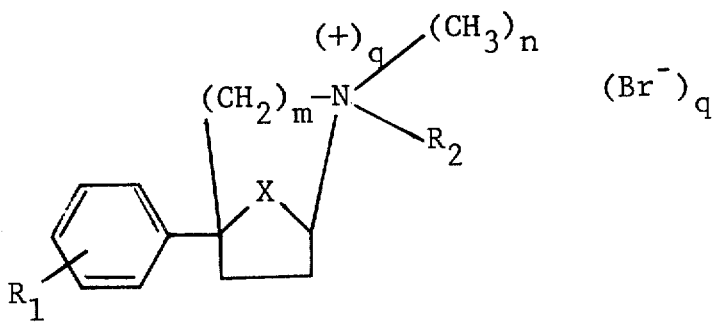

Signed and Sealed this

Twenty-second Day of August 1978

[SEAL]

Attest:

RUTH C. MASON
Attesting Officer

DONALD W. BANNER
Commissioner of Patents and Trademarks